United States Patent
Bovy et al.

(10) Patent No.: US 6,852,736 B2
(45) Date of Patent: *Feb. 8, 2005

(54) PHENOXYPROPANOLAMINES, PREPARATION AND THERAPEUTIC USE THEREOF

(75) Inventors: Philippe R. Bovy, Mareil Marly (BE); Roberto Cecchi, Lodi (IT); Olivier Venier, Saint Mande (FR)

(73) Assignee: Sanofi-Synthelabo, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/149,626

(22) PCT Filed: Dec. 15, 2000

(86) PCT No.: PCT/FR00/03559

§ 371 (c)(1),
(2), (4) Date: Jun. 12, 2002

(87) PCT Pub. No.: WO01/44227

PCT Pub. Date: Jun. 21, 2001

(65) Prior Publication Data

US 2003/0105135 A1 Jun. 5, 2003

(30) Foreign Application Priority Data

Dec. 17, 1999 (FR) .............................. 99 15933

(51) Int. Cl.$^7$ .................... A61K 31/445; C07D 401/06; C07D 211/06
(52) U.S. Cl. ................ 514/318; 514/329; 514/331; 546/193; 546/223; 546/232; 549/512
(58) Field of Search ............... 514/318, 329, 514/331; 546/193, 223, 232; 549/512

(56) References Cited

U.S. PATENT DOCUMENTS 5,627,196 A  5/1997  Hibschman et al.

FOREIGN PATENT DOCUMENTS

| DE | 35 24 955 A | 1/1986 |
| EP | 0 095 454 A | 11/1983 |
| WO | WO 99 65895 A | 12/1999 |

OTHER PUBLICATIONS

Cecchi et al. "Phenoxypropanolamines as . . . " CA 132:35618, see RN 252577–90–5 (1999).*
Spatola et al. "Amide bond surrogates . . . " Tetrahedron v. 44 p. 821–826(1988).*
Fisher et al. "Substituted sulfonamides . . . " CA 125:221588 (1996).*
Brazzell et al. "Treatment of glaucoma . . . " CA 126:1213 (1996).*
Derwent Patent Abstract No. 198349 (2002).
Derwent Patent Abstract No. 198605 (2002).
Derwent Patent Abstract No. 200011 (2002).

* cited by examiner

Primary Examiner—Celia Chang
(74) Attorney, Agent, or Firm—Michael D. Alexander

(57) ABSTRACT

The invention concerns phenoxypropanolamines of formula (I)

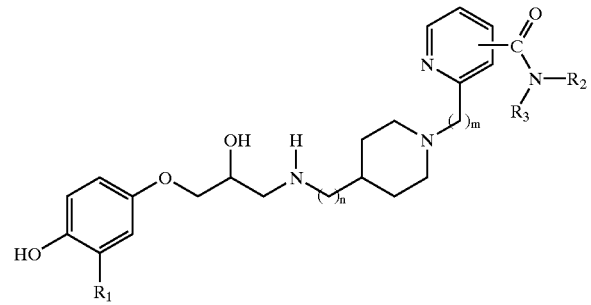

in which $R_1$ represents a hydrogen, a group —S(O)$_z$—(C$_1$–C$_4$)alk-R', (R' being H, phenyl or (C$_1$–C$_4$)alkoxy), —NHSO$_2$—(C$_1$–C$_4$)alk or NHCO(C$_1$–C$_4$)alk; m and n are each independently 0, 1 or 2; $R_2$ and $R_3$ independently represent a hydrogen, a (C$_5$–C$_6$)alkyl, (C$_3$–C$_6$)cycloalkyl, (C$_1$–C$_4$)alkoxy, hydrogen(C$_1$–C$_4$)alkoxy-(C$_1$–C$_4$)alkyl, mono- or di(C$_1$–C$_4$)alkamino(C$_1$–C$_4$)alkyl, pyrrolidino (C$_1$–C$_4$)alkyl, phenylamino or (C$_2$–C$_4$)alkenyl group, an aromatic or heteroaromatic group optionally substituted with a group $R_4$, an aralkyl or heteroaralkyl group optionally substituted with a group $R_4$, $R_2$ and $R_3$ can also together constitute a saturated or unsaturated ring of 3 to 8 atoms possibly bearing a (C$_1$–C$_4$)alkyl, amino (C$_1$–C$_4$)alkyl, carbamoyl or benzyl substituent; $R_4$ represents a hydrogen or a halogen, or a group —CO(C$_1$–C$_4$)alk or a group —NHSO$_2$—(C$_1$–C$_4$)alk; a group (C$_1$–C$_4$)alk, a group (C$_1$–C$_4$)alkoxy, a halogen, —COOH, —COO(C$_1$–C$_4$)alk, —CN, —CONR$_3$R$_4$, —NO$_2$, —SO$_2$NH$_2$ or —NHSO$_2$(C$_1$–C$_4$)alk; z is 1 or 2; and the salts or solvates thereof. The compounds have agonist activity toward β-3 adrenergic receptors.

13 Claims, No Drawings

PHENOXYPROPANOLAMINES, PREPARATION AND THERAPEUTIC USE THEREOF

The present invention relates to novel phenoxypropanolamines, to pharmaceutical compositions containing them, to a process for preparing them and to intermediates in this process.

BE 902 897 describes aryloxypropanolamines bearing a 4-piperid-1-yl group substituted on the amine, these compounds having $\beta_1$-blocker and $\alpha$-blocker activity.

J. Org. Chem., 1988, 63:889:894 describes other aryloxypropanolamines bearing a 4-piperid-1-yl group substituted on the amine.

It has now been found that phenoxypropanolamines bearing a 1-(2-pyridyl)-4-piperidyl radical on the amine have agonist activity toward $\beta_3$-adrenergic receptors.

Thus, according to one of its aspects, the present invention relates to phenoxypropanolamines of formula (I)

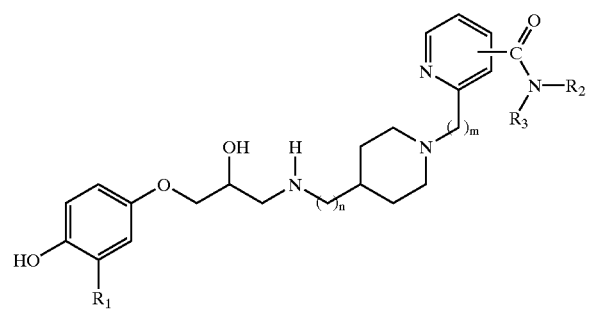

in which
- $R_1$ represents a hydrogen, a group $-S(O)_z-(C_1-C_4)$alk-R', (R' being H, phenyl or $(C_1-C_4)$alkoxy), $-NHSO_2-(C_1-C_4)$alk or NHCO $(C_1-C_4)$ alk;
- m and n are each independently 0, 1 or 2;
- $R_2$ and $R_3$ independently represent a hydrogen, a $(C_5-C_6)$ alkyl, $(C_3-C_6)$cycloalkyl, $(C_1-C_4)$alkoxy, hydroxy $(C_1-C_4)$alkyl, $(C_1-C_4)$alkoxy-$(C_1-C_4)$alkyl, mono- or di$(C_1-C_4)$alkamino$(C_1-C_4)$alkyl, pyrrolidino$(C_1-C_4)$ alkyl, phenylamino or $(C_2-C_4)$alkenyl group, an aromatic or heteroaromatic group optionally substituted with a group $R_4$, an aralkyl or heteroaralkyl group optionally substituted with a group $R_4$; $R_2$ and $R_3$ not simultaneously representing hydrogen;
- $R_2$ and $R_3$ can also together constitute a saturated or unsaturated ring of 3 to 8 atoms possibly bearing a $(C_1-C_4)$alkyl, amino$(C_1-C_4)$alkyl, carbamoyl or benzyl substituent;
- $R_4$ represents a hydrogen or a halogen, a group $-CO$ $(C_1-C_4)$alk or a group $-NHSO_2-(C_1-C_4)$alk; a group $(C_1-C_4)$alk, a group $(C_1-C_4)$alkoxy, $-COOH$, $-COO$ $(C_1-C_4)$alk, $-CN$, $-CONR_3R_4$, $-NO_2$, $-SO_2NH_2$ or $-NHSO_2(C_1-C_4)$alk;
- z is 1 or 2;
- and the salts or solvates thereof.

In the present description, the term "$(C_1-C_4)$alk" denotes a monovalent radical of a saturated $C_1-C_4$ hydrocarbon with a straight or branched chain. In the present description, the term "aralkyl" denotes a saturated divalent alkyl radical with a straight or branched chain bearing an aromatic nucleus. In the present description, the term "heteroaralkyl" denotes a saturated divalent alkyl radical with a straight or branched chain bearing a heteroaromatic nucleus.

The salts of the compounds of formulae (I) and (Ia) according to the present invention comprise not only the addition salts with pharmaceutically acceptable mineral or organic acids such as the hydrochloride, hydrobromide, sulfate, hydrogen sulfate, dihydrogen phosphate, citrate, maleate, tartrate, fumarate, gluconate, methanesulfonate, 2-naphthalene-sulfonate, etc., but also the addition salts that allow a suitable separation or crystallization of the compounds of formula (I) or (Ia), such as the picrate or the oxalate, or addition salts with optically active acids, for example camphorsulfonic acids and mandelic acids or substituted mandelic acids.

Furthermore, when the compounds of formula (I) contain a free carboxyl group, the salts also comprise the salts with mineral bases, preferably those with alkali metals such as sodium or potassium, or with organic bases.

The optically pure stereoisomers, and the mixtures of isomers of the compounds of formula (I), due to the asymmetric carbons or to the sulfinyl group in the meaning of $R_1$, in any proportion, form part of the present invention.

Preferred compounds of the present invention comprise the compounds of formula (I) in which the group $CONR_2R_3$ is in position 5 of the pyridine.

Other preferred compounds are those in which m is zero.

The compounds of formula (I) may be prepared by treating a compound of formula (II):

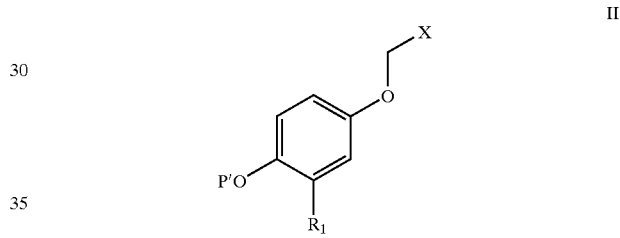

in which $R_1$ is as indicated above, P' is a protecting group and X is a group of formula (a) or (b)

(a)

(b)

in which Gp is a leaving group such as tosylate, mesylate or a halogen, with an amine of formula (III)

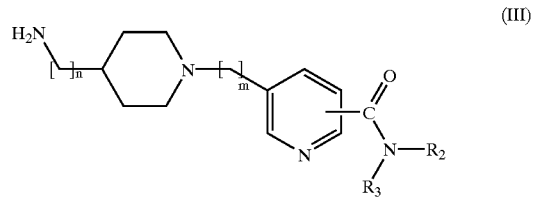

in which n, m and $CONR_2R_3$ are as defined above, by cleaving the group P' according to the usual methods and optionally transforming the compound of formula (I) thus obtained into a salt thereof.

More particularly, the reaction between the compounds of formulae (II) and (III) is performed in an organic solvent, such as a lower alcohol, for instance methanol, ethanol or isopropanol; dimethyl sulfoxide; a linear or cyclic ether; an amide, for instance dimethylformamide or dimethylacetamide; using at least equimolar amounts of the reagents, optionally with a small excess of amine.

The reaction temperature is between room temperature and the reflux point of the chosen solvent.

Protecting groups P' that may be used include the usual protecting groups for hydroxyl groups, such as, for example, methoxyethoxymethyl (MEM) or benzyl.

The cleavage of these protecting groups is carried out according to the usual methods for the chosen protecting group; in the case of the benzyl group, for example, by hydrogenation in the presence of a catalyst such as Pd/C in a suitable solvent; in the case of methoxyethoxymethyl (MEM), on the other hand, it is possible to use an acid such as trifluoroacetic acid.

Most of the epoxides of formula (II) are known literature compounds or they may be prepared by processes similar to those described in the literature. Some of the epoxides of formula (II) are described, for example, in WO 96/04233 and in U.S. Pat. No. 4,396,629. According to these methods, other epoxides of formula (II) in which $R_1$ is a group $S(O)(C_1-C_4)$alk-R' may be prepared from phenols of formula (IV).

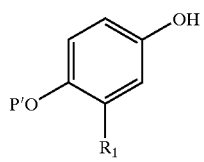
(IV)

The phenols of formula (IV) may be prepared by selective deprotection of the compounds of formula (V) in which $R_5$ represents a group $(C_2-C_4)$alk-R' and P' represents a protecting group such as methoxyethoxymethyl (MEM) or para-methoxybenzyl (pMB). The cleavage of these protecting groups is carried out according to the usual methods known to those skilled in the art for the chosen protecting group; in the case of para-methoxybenzyl (pMB), an acid such as trifluoroacetic acid may be used.

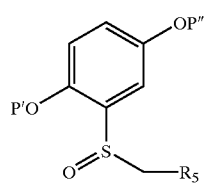
(V)

The compounds of formula (V) may be prepared by alkylating compounds of formula (VI) using a strong base, in the presence of an alkylating agent; for example, using lithium diisopropylamide and methyl iodide in tetrahydrofuran at $-50°$ C.

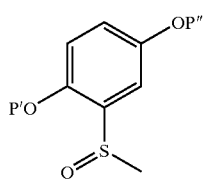
(VI)

The compounds of formula (VI) may be prepared by protecting the phenol function of compounds of formula (VII), in which P" represents a protecting group such as methoxyethoxymethyl (MEM) or para-methoxybenzyl (pMB); for example, by the action of para-methoxybenzyl chloride in the presence of a base such as sodium hydride, in a solvent, for instance dimethylformamide.

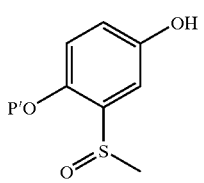
(VII)

Most of the phenols of formula (VII) are known literature compounds or may be prepared by processes similar to those described in the literature. Some of the phenols of formula (VII) are described, for example, in WO 96/04233 and in US 4 396 629.

The amines of formula (III) may be prepared by reacting suitable pyridines of formula (VIIIa) or (VIIIb)

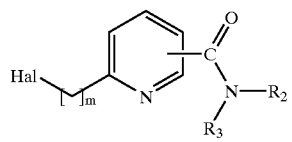
VIIIa

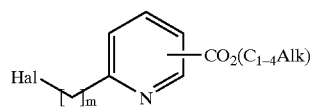
VIIIb in which Hal represents a halogen and $CONR_2R_3$ and m are as defined above, with a piperidine of formula (IX) below

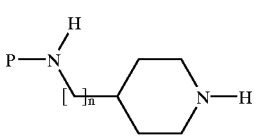
(IX)

in which n is as defined above and P represents a protecting group, in an organic solvent in the presence of a base, followed by cleavage of the group P from the compounds of formula (X) thus obtained.

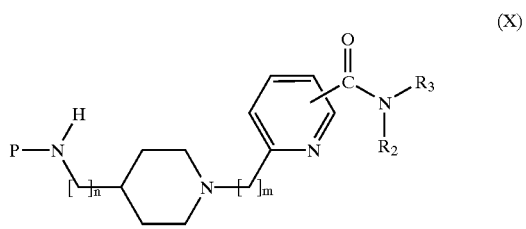

(X)

The amide group $CONR_2R_3$ is introduced onto the pyridine by forming an amide bond between a carboxylic acid and the suitable amine, optionally protected on the functional groups that might interfere, in the presence of a coupling agent such as 1-[3-(dimethyl-amino)propyl]-3-ethylcarbodiimide (DCI), dicyclohexylcarbodiimide (DCC), 1-hydroxybenzotriazole (HOBt) or (benzotriazol-1-yloxy) tris(dimethylamino)-phosphonium hexafluoriphosphate (BOP).

Reaction solvents that may be used include, for example, dimethylformamide, pyridine, dimethyl sulfoxide, a linear or cyclic ether or a chlorinated solvent such as dichloromethane.

Examples of bases that may be used include an alkali metal hydroxide, an alkali metal carbonate such as potassium carbonate or a tertiary amine such as triethylamine.

The above condensation reaction is complete within a few hours, normally within 2–12 hours.

The reaction temperature is between room temperature and the reflux point of the chosen solvent.

Protecting groups P that may be used include the usual protecting groups for amines, such as, for example, tert-butoxycarbonyl, acetyl and carbobenzyloxy.

The cleavage of these protecting groups is carried out according to the usual methods described depending on the chosen protecting group; in the case of tert-butoxycarbonyl, for example, the cleavage is normally carried out by acid hydrolysis.

Moreover, the compounds of formula (I) may be prepared by treating the acid of formula (XI):

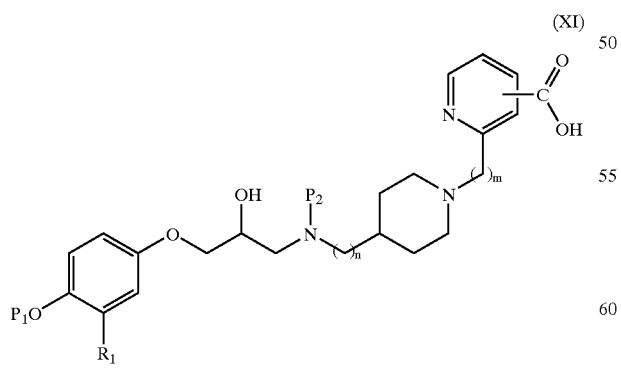

(XI)

in which n, m and $R_1$ are as defined above, $P_1$ and $P_2$ are protecting groups, with an amine of formula (XII) in the presence of a coupling agent,

(XII)

in which $R_2$ and $R_3$ are as defined above, by cleaving the groups $P_1$ and $P_2$ according to the usual methods and optionally by converting the compound of formula (I) thus obtained into a salt thereof.

More particularly, the reaction between the compounds of formulae (XI) and (XII) is performed in an organic solvent, such as dimethylformamide, pyridine, dimethyl sulfoxide, a linear or cyclic ether or a chlorinated solvent such as dichloromethane.

In the presence of a coupling agent such as DCI, DCC, EDCI, HOBt or BOP.

Examples of bases that may be used include an alkali metal hydroxide, an alkali metal carbonate such as potassium carbonate or a tertiary amine such as triethylamine.

The formation of the above amide is complete within a few hours, normally within 12–24 hours.

The reaction temperature is between room temperature and the reflux point of the chosen solvent.

Protecting groups $P_1$ that may be used include the usual protecting groups for hydroxyl groups, such as, for example, methoxyethoxymethyl (MEM) or benzyl.

The cleavage of these protecting groups is carried out according to the usual methods for the chosen protecting group; in the case of the benzyl group, for example, by hydrogenation in the presence of a catalyst such as Pd/C in a suitable solvent; on the other hand, in the case of methoxyethoxymethyl (MEM), an acid such as trifluoroacetic acid may be used.

Protecting groups $P_2$ that may be used include the usual protecting groups for amines, such as, for example, tert-butoxycarbonyl, acetyl or carbobenzyloxy.

The cleavage of these protecting groups is carried out according to the usual methods described for the chosen protecting group; for example, in the case of tert-butoxycarbonyl, the cleavage is normally carried out by acid hydrolysis.

The acids of formula (XI) may be prepared by hydrolyzing the esters (XIII) in which $R_6$ represents a $C_{1-4}$ alkyl group, according to methods known to those skilled in the art, for example by treatment with a base such as sodium hydroxide in a solvent mixture such as methanol, water and tetrahydrofuran.

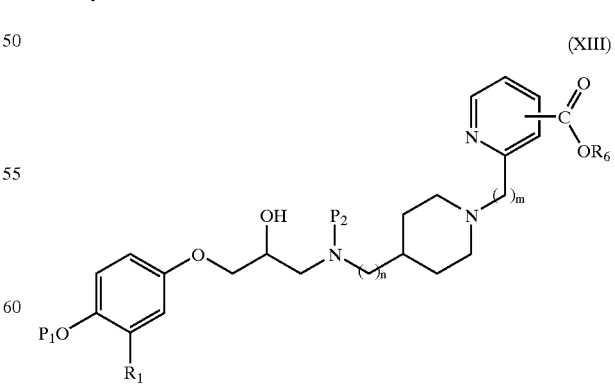

(XIII)

The esters of formula (XIII) may be prepared by protecting the secondary amine function of the esters (XIV) in which $R_6$ represents a $C_{1-6}$ alkyl group, according to methods known to those skilled in the art, for example by the action of di-tert-butyl dicarbonate in a solvent such as ethyl acetate.

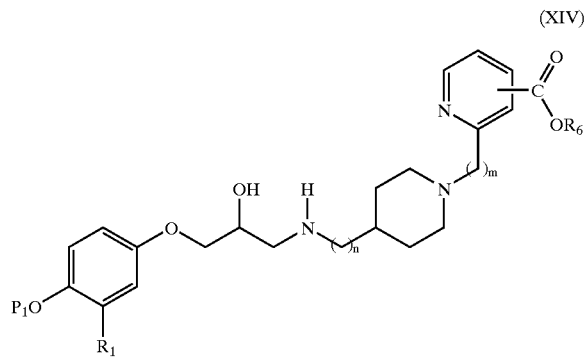

The preparation of the esters of formula (XIV) is described in WO 99/65895.

The compounds of formula (I) have shown very powerful affinity toward $\beta_3$ receptors.

The activity of the compounds of the present invention with respect to $\beta_3$ activity was demonstrated by means of in vitro tests on human colon according to the method described in EP-B-436 435 and in T. Croci et al., Br. J. Pharmacol., 1997, 122: 139P.

More particularly, it has been found that the compounds of formula (I) are much more active on isolated colon than on atrium or trachea.

These surprising properties of the compounds of formula (I) make it possible to envision their use as medicinal products with $\beta_3$action.

Furthermore, the compounds of formula (I) are relatively nontoxic; in particular, their acute toxicity is compatible with their use as medicinal products for treating diseases in which the compounds with affinity for the $\beta_3$ receptor find their application. The compounds of formula (I), and also the pharmaceutically acceptable salts thereof, may thus be indicated, for example, in the treatment of gastrointestinal diseases such as irritable bowel syndrome, as modulators of intestinal motility, as lipolytic agents, anti-obesity agents, antidiabetics, psychotropic agents, anti-glaucoma agents, cicatrizing agents, antidepressants, as uterine contraction inhibitors, as tocolytics for preventing or retarding premature labor, and for the treatment and/or prophylaxis of dysmenorrhea.

The use of the compounds of formula (I) above, and also that of the pharmaceutically acceptable salts and solvates thereof for the preparation of the above medicinal products, constitutes a further aspect of the present invention.

For such a use, an effective amount of a compound of formula (I) or of one of the pharmaceutically acceptable salts and solvates thereof is administered to mammals requiring such a treatment.

The compounds of formula (I) above and the pharmaceutically acceptable salts and solvates thereof may be used at daily doses of from 0.01 to 20 mg per kilo of body weight of the mammal to be treated, and preferably at daily doses of 0.1 to 10 mg/kg. In humans, the dose may preferably range from 0.5 mg to 1 500 mg per day and especially from 2.5 to 500 mg depending on the age of the individual to be treated, the type of treatment, prophylactic or curative, and the seriousness of the complaint. The compounds of formula (I) are generally administered in a dosage unit of 0.1 to 500 mg and preferably from 0.5 to 100 mg of active principle, one to five times a day.

Said dosage units are preferably formulated in pharmaceutical compositions in which the active principle is mixed with a pharmaceutical excipient.

Thus, according to another of its aspects, the present invention relates to pharmaceutical compositions containing, as active principle, a compound of formula (I) above or a pharmaceutically acceptable salt or solvate thereof.

In the pharmaceutical compositions of the present invention for oral, sublingual, subcutaneous, intramuscular, intravenous, topical, transdermal or rectal administration, the active ingredients of formula (I) above, and the pharmaceutically acceptable salts and solvates thereof, may be administered in unit administration forms, as a mixture with standard pharmaceutical supports, to animals and human beings, for the treatment of the abovementioned complaints. The suitable unit administration forms comprise oral forms such as tablets, gel capsules, powders, granules and oral solutions and suspensions, sublingual and buccal administration forms, subcutaneous, intramuscular or intravenous administration forms, local administration forms and rectal administration forms.

When a solid composition in the form of tablets is prepared, the main active ingredient is mixed with a pharmaceutical vehicle such as gelatin, starch, lactose, magnesium stearate, talc, gum arabic or the like. The tablets may be coated with sucrose or other suitable materials or alternatively they may be treated such that they have a sustained or delayed activity and such that they release a predetermined amount of active principle continuously.

A preparation in gel capsules is obtained by mixing the active ingredient with a diluent and pouring the mixture obtained into soft or hard gel capsules.

A preparation in the form of a syrup or elixir may contain the active ingredient in combination with a sweetener, preferably a calorie-free sweetener, methylparaben and propylparaben as antiseptics, and also a flavoring agent and a suitable colorant.

The water-dispersible powders or granules may contain the active ingredient as a mixture with dispersants or wetting agents, or suspension agents, for instance polyvinylpyrrolidone, and also with sweeteners of or flavor enhancers.

For local administration, the active principle is mixed in an excipient for the preparation of creams or ointments or is dissolved in a vehicle for intraocular administration, for example in the form of eye drops.

For rectal administration, use is made of suppositories which are prepared with binders that melt at the rectal temperature, for example cocoa butter or polyethylene glycols.

For parenteral administration, aqueous suspensions, saline solutions or sterile injectable solutions which contain pharmacologically compatible dispersants and/or wetting agents, for example propylene glycol or butylene glycol, are used.

The active principle may also be formulated in the form of microcapsules, optionally with one or more supports or additives.

According to another of its aspects, the present invention relates to a method for treating pathologies that are improved with a $\beta_3$-agonist action, which comprises administering a compound of formula (I) or a pharmaceutically acceptable salt or solvate thereof.

The compounds of formula (I), especially the compounds (I) labeled with an isotope, may also be used as laboratory tools in biochemical tests.

The compounds of formula (I) bind to the $\beta_3$-adrenergic receptor. These compounds may thus be used in an ordinary binding test, in which an organic tissue in which this receptor is particularly abundant is used, and the amount of compound (I) displaced with a test compound is measured, to assess the affinity of said compound for the binding sites of this particular receptor.

Another specific subject of the present invention is thus a reagent that may be used in biochemical tests, which comprises at least one suitably labeled compound of formula (I).

The examples that follow illustrate the invention more clearly. The mass spectra (not indicated) and also the molecular ions $[M+H]^+$ confirm the structure of the compounds.

PREPARATION 1

4-tert-Butoxycarbonylaminopiperidine 25 g (0.13 mol) of 4-amino-1-benzylpiperidine, 36.2 ml (0.26 mol) of triethylamine and 31.2 g (0.143 mol) of di-tert-butyl dicarbonate in 200 ml of dimethylformamide are mixed together at room temperature for 2 hours. The mixture is poured into water, extracted with ethyl acetate and washed with water, and the product thus obtained is crystallized from 200 ml of isopropyl ether. 33 g of 1-benzyl-4-tert-butoxycarbonylaminopiperidine are obtained, and are hydrogenated in a mixture of 200 ml of ethanol and 100 ml of tetrahydrofuran in the presence of 3 g of 10% Pd/C. After filtering off the catalyst, the title compound is isolated. m.p. 157–160° C.

PREPARATION 2

4-tert-Butoxycarbonylamino-1-(5-aminocarbonyl-2-pyridyl)piperidine

A mixture of 3 g (0.015 mol) of the product of preparation 1, 1.5 g (0.015 mol) of triethylamine and 2.34 g (0.015 mol) of 6-chloronicotinamide in 60 ml of dimethylformamide is heated at 80° C. for 18 hours. After cooling, water is added and the product is filtered off. 2.8 g of the title compound are thus obtained. m.p. 255° C. dec.

PREPARATON 3

4-Amino-1-(5-aminocarbonyl-2-pyridyl)piperidine and its Dihydrochloride Semihydrate 1.84 g (0.0057 mol) of the product of example 1 and 50 ml of ethyl acetate are mixed together. 50 ml of a 3 N solution of hydrochloric acid in ethyl acetate are added thereto with stirring and stirring is continued at room temperature for 10 hours. The product is filtered off and washed with acetone. 1.67 g of the title compound are thus obtained.

m.p. 290° C. dec.

PREPARATION 4

4-tert-Butoxycarbonylamino-1-(5-ethoxycarbonyl-2-pyrldyl)piperidine.

A mixture as described in preparation 1, but using ethyl 6-chioronicotinate instead of 6-chioronicotinamide, is reacted. After cooling, water is added thereto, the mixture is extracted with ethyl acetate, the organic phase is dried over sodium sulfate and the solvent is evaporated off under reduced pressure. The title compound is obtained. m.p. 140–142° C.

PREPARATION 5

4-Amino-1-(5-ethoxycarbonyl-2-pyrldyl)plperidine and the dihydrochioride hydrate thereof Working as described in preparation 3, but using the product of preparation 4 instead of the product of preparation 3, the title compound is obtained. m.p. 148–150° C.

PREPARATION 6

(2S)-4-Benzyloxy-3-methylsulfinyl-1-(2,3-epoxypropoxy)-benzene 0.71 g of 60% NaH (0.0177 mol) is dissolved, with stirring and under a nitrogen atmosphere, in 15 ml of dimethylformamide, 4.45 g (0.0169 mol) of 4-benzyloxy-3-methylsulfinylphenol (prepared according to the process described in U.S. Pat. No. 4,396,629) in 35 ml of dimethylformamide are added slowly (over 30 minutes), followed by addition of 4.40 g (0.0169 mol) of S(+)glycildylnosilate in 10 ml of dimethylformamide. After introducing this last reagent, the mixture is left to react at room temperature for 3 hours. Water is added, the mixture is extracted with ethyl acetate and the solvent is evaporated off. The crude reaction product is purified by flash chromatography, eluting with a 97/3 $CH_2Cl_2$/MeOH mixture. $[\alpha]_{365nm}=-14.3°$; $[\alpha]_{436nm}=-3.9°$ (C=1% in $CH_3OH$, t=20°). The title compound is obtained.

The product thus obtained is subjected to an HPLC analysis under the following conditions:

—chiral stationary phase: CHIRALCEL OD-H

—mobile phase: 80/20 hexane/ethanol (0.5 ml/min).

Two peaks are observed at $RT_1$=20.780 min and $RT_2$= 23.900 min corresponding to the diastereoisomers having a different configuration at the sulfur atom.

PREPARATION 7

4-tert-Butoxycarbonylamino-1-(5-hydroxycarbonyl-2-pyridyl)piperidine

A solution of 1.88 g of 4-tert-butoxy-carbonylamino-1-(5-ethoxycarbonyl-2-pyridyl)piperidine (5.4 mmol) in a mixture of 80 ml of methanol, 90 ml of molar aqueous sodium hydroxide solution and 30 ml of tetrahydrofuran is stirred for 26 hours and then acidified to pH 6 with molar aqueous hydrochloric acid solution. The solution is then basified to pH 8 with saturated aqueous sodium carbonate solution. The organic solvents are evaporated off under reduced pressure and the aqueous solution is acidified to pH 4 with aqueous 10% citric acid solution. The precipitate formed is filtered off and then washed with cold methanol to give 4-tert-butoxycarbonylamino-1-(5-hydroxycarbonyl-2-pyridyl)piperidine in the form of a beige-colored solid (1.75 g, 100%). $[M+H^+]$=322.4

PREPARATION 8

4-tert-Butoxycarbonylamino-1-(5-piperid-1-ylcarbonyl-2-pyridyl)piperidine

A solution of 0.4 g of 4-tert-butoxycarbonyl-amino-1-(5-hydroxycarbonyl-2-pyridyl)piperidine (1.24 mmol), 0.826 g of benzotriazol-1-yloxytris-(dimethylamino)phosphonium hexafluorophosphate (1.86 mmol), 0.408 ml of piperidine (3.72 mmol) and 0.4 ml of triethylamine in 8 ml of dichloromethane is stirred for 4 hours. Water is added and the aqueous phase is extracted three times with dichloromethane. The organic phases are dried over magnesium sulfate and concentrated under reduced pressure. The 4-tert-butoxycarbonylamino-1-(5-piperid-1-ylcarbonyl-2-pyridyl)piperidine is obtained in the form of an oil (0.475 g, 98%) after purification on silica gel (eluent: 96/4 dichloromethane/methanol). [M+H$^+$]=389.3

PREPARATION 9

4-Amino-1-(5-piperid-1-ylcarbonyl-2-pyridyl)piperidine

A solution of 0.475 g of 4-tert-butoxycarbonylamino-1-(5-piperid-1-ylcarbonyl-2-pyridyl)piperidine (1.24 mmol) and 5 ml of trifluoroacetic acid in 20 ml of dichloromethane is stirred for 1 hour. The reaction medium is concentrated under reduced pressure and then taken up in dichloromethane. The solution is basified (pH=9) using saturated aqueous sodium carbonate solution. The aqueous phase is extracted five times with dichloromethane. The organic phases are dried over magnesium sulfate and concentrated under reduced ressure. The 4-amino-1-(5-piperid-1-ylcarbonyl-2-pyridyl)piperidine is obtained in the form of an oil (0.310 g, 88%). [M+H$^+$]=289.4

PREPARATION 10

3-[1-(5-Piperid-1-ylcarbonyl-2-pyridyl)-4-piperidylamino]-1-[(4-benzyloxy-3-methylsulfinyl)phenoxy]-2-propanol A solution of 0.1 g of 4-benzyloxy-3-methylsulfinyl-1-(2,3-epoxypropoxy)benzene (0.31 mmol) and 0.173 g of 4-amino-1-(5-piperid-1-ylcarbonyl-2-pyridyl)piperidine (0.62 mmol) in 15 ml of ethanol is refluxed for 17 hours and the reaction medium is then concentrated under reduced pressure. The 3-[1-(5-piperid-1-ylcarbonyl-2-pyridyl)-4-piperidylamino]-1-[(4-benzyloxy-3-methylsulfinyl)phenoxy]-2-propanol is obtained in the form of an oil (0.140 g, 73%) after purification on silica gel (eluent: 95/5 dichloromethane/methanol). [M+H$^+$]=607.5

EXAMPLE 1

3-[1-(5-Piperid-1-ylcarbonyl-2-pyridyl)-4-piperidylamino]-1-[(4-hydroxy-3-methylsulfinyl)phenoxy]-2-propanol and the tris(trifluoroacetate) Thereof A solution of 0.14 g of 3-[1-(5-piperid-1-ylcarbonyl-2-pyridyl)-4-piperidylamino]-1-[(4-benzyl-oxy-3-methylsulfinyl)phenoxy]-2-propanol and the tris(trifluoroacetate) Thereof (0.31 mmol) in 4 ml of trifluoroacetic acid is heated for 6 hours at 65° C. and the reaction medium is then concentrated under reduced pressure. The 3-[1-(5-piperid-1-ylcarbonyl-2-pyridyl)-4-piperidylamino]-1-[(4-hydroxy-3-methylsulfinyl)phenoxy]-2-propanol is obtained in the form of the tris(trifluoroacetate) (0.1 g, 50%) after purification on preparative HPLC/MS and evaporation of the solvents.
Apparatus: Two Shimatzu LC8 pumps coupled to an API 100 PE sciex mass spectrometer. An SCL-10A controller. A Gilson 215 fraction injector-collector.
Stationary Phase:
  YMC-Guardpack ODS, 50×20 mm, S-5 µm, 120 A
Mobile Phase
  Eluent A: 95/5 H$_2$O/MeOH+0.05% CF$_3$COOH
  Eluent B: 5/95 H$_2$O/MeOH+0.05% CF$_3$COOH
  Flow rate: 30 ml/min Elution Gradient:

| t (in min) | % A | % B |
|---|---|---|
| 0 | 90 | 10 |
| 3 | 90 | 10 |
| 11 | 10 | 90 |
| 13 | 10 | 90 |

RT=6.05 min [M+H$^+$]=517.4.

The purified product was analyzed by HPLC under the following conditions.
Apparatus: Two Shimatzu LC8 pumps coupled to an SPD10-A UV detector and to an API 100 PE sciex mass spectrometer. An SCL-10A controller. A Gilson 215 fraction injector-collector.
Stationary Phase:
  YMC-Pack FL-ODS, 50×4.6 mm, S-5 µm, 120 A
Mobile Phase:
  Eluent A: 95/5 H$_2$O/MeOH+0.05% CF$_3$COOH
  Eluent B: 5/95 H$_2$O/MeOH+0.05% CF$_3$COOH
  Flow rate: 3 ml/min
Elution Gradient:

| t (in min) | % A | % B |
|---|---|---|
| 0 | 90 | 10 |
| 1 | 90 | 10 |
| 9 | 10 | 90 |
| 10 | 10 | 90 |

RT=4.07 min [M+H$^+$]=517.4.

EXAMPLE 2

3-[1-(5-Benzylaminocarbonyl-2-pyridyl)-4-piperidyl-amino]-1-[(4-hydroxy-3-methylsulfinyl)phenoxy]-2-propanol and the tris(trifluoroacetate) Thereof Working as described in example 1, but using 4-amino-1-(5-benzylaminocarbonyl-2-pyridyl)piperidine instead of 4-amino-1-(5-piperid-1-ylcarbonyl-2-pyridyl)piperidine in preparation 10, the title compound is obtained.
RT=4.57 min, [M+H$^+$]=539.4.

EXAMPLE 3

3-[1-[5-(3-methoxyphenyl)aminocarbonyl-2-pyridyl-1–4-piperidylamino]-1-[(4-hydroxy-3-methylsulfinyl)-phenoxy]-2-propanol and the tris(trifluoroacetate) thereof Working as described in example 1, but using 4-amino-1-[5-(3-methoxyphenyl)aminocarbonyl-2-pyridyl]piperidine instead of 4-amino-1-(5-piperid-1-ylcarbonyl-2-pyridyl)piperidine in preparation 10, the title compound is obtained.
RT=4.93 min, [M+H$^+$]=555.3.

EXAMPLE 4

3-[1-[5-Benzylaminocarbonyl-2-pyridyl]-4-piperidyl-aminomethyl]-1-[(4-hydroxy-3-methylsulfinyl)phenoxy]-2-propanol and the tris(trifluoroacetate) Thereof Working as described in example 2, but using 4-aminomethyl-1-benzylpiperidine instead of 4-amino-1- benzylpiperidine in preparation 1, the title compound is obtained. RT=4.81 min, [M+H$^+$]=553.2.

EXAMPLE 5

3-[1-[5-Piperid-1-ylcarbonyl-2-pyridyl]-4-piperidyl-aminomethyl]-1-[(4-hydroxy-3-methylsulfinyl) phenoxy]-2-propanol and the tris(trifluoroacetate) Thereof Working as described in example 1, but using 4-aminomethyl-1-benzylpiperidine instead of 4-amino-1-benzylpiperidine in preparation 1, the title compound is obtained. RT=4.16 min, [M+H$^+$]=531.3.

EXAMPLE 6

3-[1-[5-(3-Methoxyphenyl)aminocarbonyl-2-pyridyl]-4-piperidylaminomethyl]-1-[(4-hydroxy-3-methylsulfinyl)phenoxy]-2-propanol and the tris (trifluoroacetate) Thereof Working as described in example 3, but using 4-aminomethyl-1-benzylpiperidine instead of 4-amino-1-benzylpiperidine in preparation 1, the title compound is obtained. RT=5.10 min, [M+H$^+$]=569.4.

PREPARATION 11

3-[1-[5-Ethoxycarbonyl-2-pyridyl]-4-piperidyl-tert-butoxycarbonylaminomethyl]-1-[(4-benzoxy-3-methylsulfinyl)phenoxy]-2-propanol A solution of 0.9 g of 3-[1-[5-ethoxy-carbonyl-2-pyridyl]-4-piperidylaminomethyl]-1-[(4-benzoxy-3-methylsulfinyl) phenoxy]-2-propanol (1.55 mmol) and 0.37 g of di-tert-butyl dicarbonate (1.705 mmol) in ethyl acetate (25 ml) is refluxed for 24 hours. After cooling to room temperature and adding water, the aqueous phase is extracted twice with ethyl acetate. The organic phases are combined, and dried over magnesium sulfate, and the solvents are evaporated off under reduced pressure. The 3-[1-[5-ethoxycarbonyl-2-pyridyl]-4-piperidyl-tert-butoxycarbonylaminomethyl]-1-[(4-benzoxy-3-methylsulfinyl)phenoxy]-2-propanol is obtained in the form of a white powder (0.32 g, 30%) after purification on silica gel (25 g SiO$_2$, eluent: ½ heptane/ethyl acetate). [M+H$^+$]=682.5.

PREPARATION 12

3-[1-[5-Hydroxycarbonyl-2-pyridyl]-4-piperidyl-tert-butoxycarbonylaminomethyl]-1-[(4-benzoxy-3-methylsulfinyl)phenoxy]-2-propanol.

A solution of 5 g of 3-[1-[5-ethoxycarbonyl-2-pyridyl]-4-piperidyl-tert-butoxycarbonylaminomethyl]-1-[(4-benzoxy-3-methylsulfinyl)phenoxyl]-2-propanol (7.34 mmol) in a mixture of methanol (200 ml), tetrahydrofuran (100 ml) and aqueous 1 N sodium hydroxide solution (55 ml, 4 eq) is heated for 18 hours at 50° C. After cooling to room temperature, 1 N hydrochloric acid solution is added to pH 1, followed by addition of saturated sodium hydrogen carbonate solution to pH 8. The volatile solvents are evaporated off under reduced pressure and the aqueous phase is then extracted twice with ethyl acetate. 10% citric acid solution is added to the aqueous phase to pH 6. This aqueous phase is extracted twice with ethyl acetate and these organic phases are combined and dried over magnesium sulfate. After evaporating off the solvent under reduced pressure, 3-[1-[5-hydroxycarbonyl-2-pyridyl]-4-piperidyl-tert-butoxycarbonylaminomethyl]-1-[(4-benzoxy-3-methylsulfinyl)]-2-propanol is obtained in the form of a white solid (4.36 g, 91%). [M+H$^+$]=654.6.

EXAMPLE 7

3-[1-[5-(Morphol-4-yl)carbonyl-2-pyridyl]-4-piperidyl-aminomethyl]-1-[(4-hydroxy-3-methylsulfinyl)phenoxyl]-2-propanol and the tris (trifluoroacetate) thereof A solution of 0.1 g of 3-[1-[5-hydroxycarbonyl-2-pyridyl]-4-piperidyl-tert-butoxycarbonylaminomethyl]-1-[(4-benzoxy-3-methylsulfinyl)phenoxy]-2-propanol (0.15 mmol) 0.04 g of 1-hydroxybenzotriazole (0.3 mmol), 0.06 g of 1-ethyl-3-(3-dimethylaminopropyl)carbodiimide (0.3 mmol), 0.45 ml of triethylamine and 0.04 ml of morpholine (0.45 mmol) in 10 ml of dichloromethane is stirred for 21 hours. Water is added and the organic phase is washed three times with water. The organic phases are dried over magnesium sulfate and concentrated under reduced pressure. The crude reaction product is then heated for 7 hours at 60° C in 5 ml of trifluoroacetic acid, and the reaction medium is then concentrated under reduced pressure. The 3-[1-[5-(morphol-4-yl)carbonyl-2-pyridyl]-4-piperidyl-aminomethyl]-1-[(4-hydroxy-3-methylsulfinyl)phenoxy]-2-propanol is obtained in the form of the tris(trifluoroacetate) (0.20 g, 17%) after purification on preparative HPLC/MS and evaporation of the solvents.

Apparatus:Two Shimatzu LC8 pumps coupled to an API 100 PE sciex mass spectrometer. An SCL-10A controller. A Gilson 215 fraction injector-collector.

Stationary Phase:

YMC-Guardpack ODS, 50×20 mm, S-5 µm, 120 A

Mobile Phase:

Eluent A: 95/5 H$_2$O/MeOH+0.05% CF$_3$COOH

Eluent B: 5/95 H$_2$O/MeOH+0.05% CF$_3$COOH

Flow rate: 30 ml/min

Elution Gradient:

| t (in min) | % A | % B |
|---|---|---|
| 0 | 90 | 10 |
| 3 | 90 | 10 |
| 11 | 10 | 90 |
| 13 | 10 | 90 |

RT=4.81 min [M+H$^+$]=533.7.

The purified product was analyzed by HPLC under the following conditions.

Apparatus: Two Shimatzu LC8 pumps coupled to an SPD10-A UV detector and an API 100 PE sciex mass spectrometer. An SCL-10A controller. A Gilson 215 fraction injector-collector.

Stationary Phase:

YMC-Pack FL-ODS, 50×4.6 mm, S-5 µm, 120 A

Mobile Phase:

Eluent A: 95/5 H$_2$O/MeOH+0.05% CF$_3$COOH

Eluent B: 5/95 H$_2$O/MeOH+0.05% CF$_3$COOH

Flow rate: 3 ml/min

Elution Gradient:

| t (in min) | % A | % B |
|---|---|---|
| 0 | 90 | 10 |
| 1 | 90 | 10 |
| 9 | 10 | 90 |
| 10 | 10 | 90 |

RT=3.40 min [M+H$^+$]=533.7.

EXAMPLE 8

3-[1-[5-(2-Methoxybenzyl)aminocarbonyl-2-pyridyl]-4-piperidylaminomethyl]-1-[(4-hydroxy-3-methylsulfinyl)phenoxy]-2-propanol and the tris (trifluoroacetate) Thereof Working as described in example 4, but using 2-methoxybenzylamine instead of morpholine, the title compound is obtained.
RT=4.87 min, [M+H$^+$]=583.5.

PREPARATION 13

4-Benzyloxy-3-methylsulfinylphenol p-methoxybenzoate (pmb)

A solution of 1 g of 4-benzyloxy-3-methylsulfinylpbenol (3.85 mmol), 0.185 g of 60% sodium hydride in oil (4.6 mmol) and 0.678 ml of 4-methoxybenzyl chloride (5 romol) in 20 ml of dimethylformamide is stirred for 2 hours. Water is added and the aqueous phase is extracted twice with ethyl acetate. The organic phases are combined, dried over magnesium sulfate and the solvents are evaporated off under reduced pressure. The 4-benzyloxy 3-etbylsulfinyiphenol pmb is obtained in the form of a white solid (1.6 g, 88%) after trituration in pentane, filtration and drying under vacuum. [M+H$^+$]=383.3.

PREPARATION 14

4-Benzyloxy-3-ethylsulfinylphenol pmb

A solution of 0.4 g of 4-benzyloxy-3-methylsulfinylphenol pmb (1.05 mmol) in 40 ml of tetrahydrofuran is cooled to −50° C. and 0.784 ml of a dimolar solution of lithium diisopropylamide (1.57 mmol) in tetrahydrofuran is then added. The reaction mixture is stirred for 15 minutes and 0.13 ml of methyl iodide (1.1 mmol) is added. After stirring for 15 minutes, methanol is added and the solvents are evaporated off under reduced pressure. The 4-benzyloxy-3-ethylsulfinylphenol pmb is obtained in the form of a white solid (0.3 g, 72%) after purification on silica gel (40 g SiO$_2$, eluent: 4/1 heptane/ethyl acetate)

PREPARATION 15

4-Benzyloxy-3-ethylsulfinylphenol

A solution of 0.3 g of 4-benzyloxy-3-ethylsulfinylphenol pmb (0.75 mmol) in a mixture of 5 ml of trifluoroacetic acid and 5 ml of dichloromethane is stirred at 0° C. for 2 hours. The solvents are evaporated off under reduced pressure. The 4-benzyloxy-3-ethylsulfinylphenol (0.2 g, 95%) is obtained in the form of a white solid after purification on silica gel (10 g SiO$_2$, eluent: 1/1 heptane/ethyl acetate). [M+H$^+$]=277.4.

EXAMPLE 9

3-[1-[5-Piperid-1-ylcarbonyl-2-pyridyl]-4-piperidyl-amino]-1-[(4-hydroxy-3-ethylsulfinyl)phenoxy]-2-propanol and the tris (trifluoroacetate) thereof Working as described in example 1, but using 4-benzyloxy-3-ethylsulfinylphenol instead of 4-benzyloxy-3-methylsulfinylphenol in preparation 6, the title compound is obtained. RT=4.47 min, [M+H$^+$]=531.3

The table below illustrates the chemical sturctures and the chemical properties of some of the compounds of the examples of formula (I) according to the invention.

TABLE 1

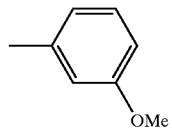

| n | m | R$_1$ | R$_2$ | R$_3$ | [M + H]$^+$ |
|---|---|---|---|---|---|
| 0 | 0 | S(O)Me | | —(CH$_2$)$_5$— | 517.4 |
| 0 | 0 | S(O)Me | H | CH$_2$—Ph | 539.4 |
| 0 | 0 | S(O)Me | H | 3-OMe-C$_6$H$_4$— | 555.3 |
| 0 | 1 | S(O)Me | H | CH$_2$—Ph | 553.2 |
| 0 | 1 | S(O)Me | | —(CH$_2$)$_5$— | 531.3 |

TABLE 1-continued

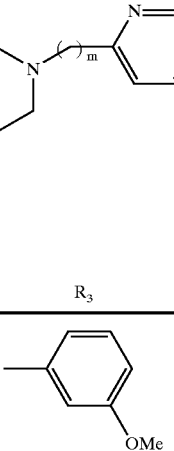

| n | m | R₁ | R₂ | R₃ | [M + H]⁺ |
|---|---|-----|-----|-----|----------|
| 0 | 1 | S(O)Me | H | 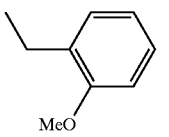 3-OMe-phenyl | 569.4 |
| 0 | 1 | S(O)Me | —(CH₂)₂—O—(CH₂)₂— | | 533.7 |
| 0 | 1 | S(O)Me | H | 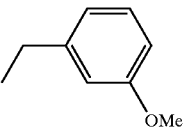 2-ethyl-6-OMe-phenyl | 583.5 |
| 0 | 0 | S(O)Et | —(CH₂)₄— | | 531.3 |
| 0 | 1 | S(O)Me | —(CH₂)₂—NH—(CH₂)₂— | | 532.5 |
| 0 | 1 | S(O)Me | —(CH₂)₂—CHMe—(CH₂)₂— | | 545.7 |
| 0 | 1 | S(O)Me | —(CH₂)₂—CH(CH₂Ph)—(CH₂)₂— | | 621.6 |
| 0 | 1 | S(O)Me | —(CH₂)₂—CH(CONH₂)—(CH₂)₂— | | 574.5 |
| 0 | 1 | S(O)Me | —(CH₂)₄— | | 517.4 |
| 0 | 1 | S(O)Me | —(CH₂)₂—CH(CH₂—NH₂)—(CH₂)₂— | | 560.4 |
| 0 | 1 | S(O)Me | —(CH₂)₂—NMe—(CH₂)₂— | | 546.6 |
| 0 | 1 | S(O)Me | H | 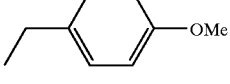 3-ethyl-4-OMe-phenyl | 583.5 |
| 0 | 1 | S(O)Me | H | 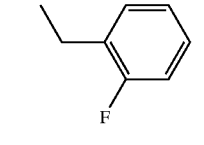 4-ethyl-?-OMe-phenyl | 583.5 |
| 0 | 1 | S(O)Me | H | 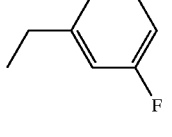 2-ethyl-3-F-phenyl | 571.5 |
| 0 | 1 | S(O)Me | H | 3-ethyl-5-F-phenyl | 571.5 |
| 0 | 1 | S(O)Me | H | 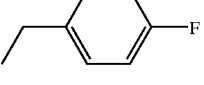 3-ethyl-4-F-phenyl | 571.5 |
| 0 | 1 | S(O)Me | H | CH₂—CH=CH₂ | 503.3 |
| 0 | 1 | S(O)Me | H | CH₂—CH₂OH | 507.5 |
| 0 | 1 | S(O)Me | H | CH₂—CH₂—OCH₃ | 521.6 |
| 0 | 1 | S(O)Me | H | OCH₃ | 493.4 |
| 0 | 1 | S(O)Me | CH₃ | OCH₃ | 507.5 |

TABLE 1-continued

| n | m | R₁ | R₂ | R₃ | [M + H]⁺ |
|---|---|----|----|----|----------|
| 0 | 1 | S(O)Me | H | -CH₂CH₂CH₂-pyrrolidinyl | 560.4 |
| 0 | 1 | S(O)Me | H | -NH-phenyl | 554.4 |
| 0 | 1 | S(O)Me | H | -CH₂CH₂CH₂-N(CH₃)₂ | 534.3 |
| 0 | 1 | S(O)Me | H | —(CH$_2$)$_4$—CH$_3$ | 533.4 |
| 0 | 1 | S(O)Me | H | —(CH$_2$)$_5$—CH$_3$ | 547.5 |
| 0 | 1 | S(O)Me | H | -CH(CH₂CH₃)₂ | 533.4 |
| 0 | 1 | S(O)Me | H | cyclopropyl | 503.3 |
| 0 | 1 | S(O)Me | H | cyclobutyl | 517.4 |
| 0 | 1 | S(O)Me | H | cyclopentyl | 531.6 |
| 0 | 1 | S(O)Me | H | cyclohexyl | 545.4 |
| 0 | 0 | S(O)npr | —(CH$_2$)$_4$— | | 545.4 |
| 0 | 0 | S(O)nBu | —(CH$_2$)$_4$— | | 559.5 |
| 0 | 0 | S(O)—(CH$_2$)$_2$—OCH$_3$ | —(CH$_2$)$_4$— | | 561.6 |
| 0 | 0 | S(O)—(CH$_2$)$_3$-Ph | —(CH$_2$)$_4$— | | 621.6 |

What is claimed is:

1. A phenoxypropanolamine of formula (I)

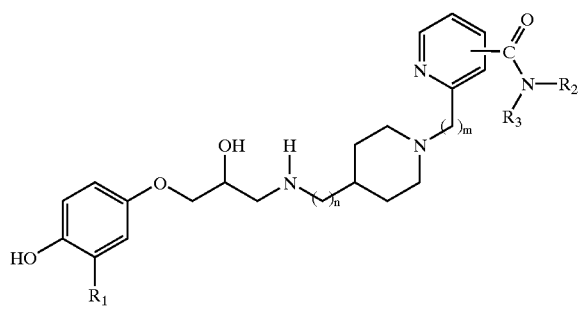

in which

R$_1$ represents a hydrogen, a group —S(O)$_z$—(C$_1$–C$_4$)alk-R', (R' being H, phenyl or (C$_1$–C$_4$)alkoxy), —NHSO$_2$—(C$_1$–C$_4$)alk or NHCO(C$_1$–C$_4$) alk;

m and n are each independently 0, 1 or 2;

R$_2$ and R$_3$ independently represent a hydrogen, a (C$_5$–C$_6$) alkyl, (C$_3$–C$_6$)cycloalkyl, (C$_1$–C$_4$)alkoxy, hydroxy (C$_1$–C$_4$)alkyl, (C$_1$–C$_4$)alkoxy-(C$_1$–C$_4$)alkyl, mono- or di(C$_1$–C$_4$)alkamino(C$_1$–C$_4$)alkyl, pyrrolidino(C$_1$–C$_4$) alkyl, phenylamino or (C$_2$–C$_4$)alkenyl group, an aromatic or heteroaromatic group optionally substituted with a group R$_4$, an aralkyl or heteroaralkyl group optionally substituted with a group R$_4$; R$_2$ and R$_3$ not simultaneously representing hydrogen;

R$_2$ and R$_3$ can also together constitute a saturated or unsaturated ring of 3 to 8 atoms possibly bearing a (C$_1$–C$_4$)alkyl, amino(C$_1$–C$_4$)alkyl, carbamoyl or benzyl substituent;

R$_4$ represents a hydrogen or a halogen, a group —CO (C$_1$–C$_4$)alk or a group —NHSO$_2$—(C$_1$–C$_4$)alk; a group (C$_1$–C$_4$)alk, a group (C$_1$–C$_4$)alkoxy, a halogen, —COOH, —COO(C$_1$–C$_4$)alk, —CN, —CONR$_3$R$_4$, —NO$_2$, —SO$_2$NH$_2$ or —NHSO$_2$(C$_1$–C$_4$)alk;

z is 1 or 2;

or a salts or solvates thereof.

2. The compound as claimed in claim 1, of formula (I) in which the group CONR$_2$R$_3$ is in position 5 on the pyridine.

3. The compound as claimed in claim 1, of formula (I) in which m is zero.

4. A process for preparing the compounds of formula (I) as claimed in claim 1, characterized in that a compound of formula (II):

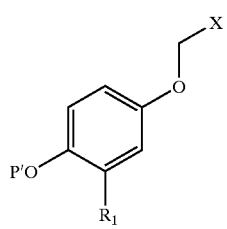

in which R$_1$ is as indicated in formula (I), P' is a protecting group and X is a group of formula (a) or (b)

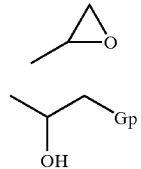

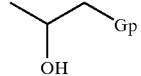

in which Gp is a leaving group such as tosylate, mesylate or a halogen, is reacted with an amine of formula (III)

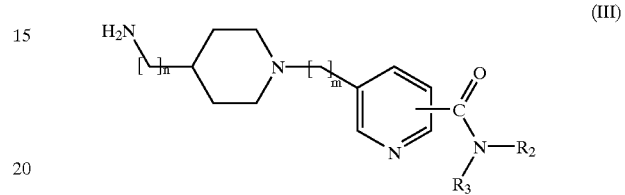

in which n, m, R$_2$ and R$_3$ are as defined in formula (I) by cleaving the group P' according to the usual methods, and optionally transforming the compound of formula (I) thus obtained into a salt thereof.

5. A pharmaceutical composition comprising, as active principle, at least one compound of formula (I) as claimed in 1, or a pharmaceutically acceptable salt thereof.

6. A pharmaceutical composition comprising, as active principle, an effective amount of at least one compound of formula (I) as claimed in claim 2, or a pharmaceutically acceptable salt thereof.

7. A pharmaceutical composition comprising, as active principle, an effective amount of at least one compound of formula (I) as claimed in claim 3, or a pharmaceutically acceptable salt thereof.

8. A method for treating irritable bowel syndrome, for treating obesity, or for treating diabetes, which comprises administering to a patient in need of such treatment an effective amount of a compound according to claim 1.

9. A method for treating irritable bowel syndrome, for treating obesity, or for treating diabetes, which comprises administering to a patient in need of such treatment an effective amount of a compound according to claim 2.

10. A method for treating irritable bowel syndrome for treating obesity, or for treating diabetes, which comprises administering to a patient in need of such treatment an effective amount of a compound according to claim 3.

11. A method according to claim 8 for the treatment of irritable bowel syndrome.

12. A method according to claim 9 for the treatment of irritable bowel syndrome.

13. A method according to claim 10 for the treatment of irritable bowel syndrome.

* * * * *